United States Patent [19]
Lokshin et al.

[11] Patent Number: 6,019,914
[45] Date of Patent: Feb. 1, 2000

[54] PHOTOCHROMIC SPIROOXAZINE COMPOUNDS, THEIR USE IN THE FIELD OF OPHTHALMIC OPTICS

[75] Inventors: Vladimir Lokshin; Karine Chamontin; Robert Guglielmetti; André Samat, all of Marseille, France

[73] Assignee: Essilor International Compagnie Generale D'Optique, Charenton Cedex, France

[21] Appl. No.: 08/926,034

[22] Filed: Sep. 9, 1997

[30] Foreign Application Priority Data

May 6, 1997 [FR] France .................................... 97 05544

[51] Int. Cl.[7] ........................ C07D 498/10; C07D 498/20
[52] U.S. Cl. ................................................ 252/586; 544/71
[58] Field of Search ................................ 544/71; 252/586

[56] References Cited

U.S. PATENT DOCUMENTS

| | | | |
|---|---|---|---|
| 4,931,220 | 6/1990 | Haynes et al. | 252/586 |
| 5,000,878 | 3/1991 | Chu | 252/587 |
| 5,114,621 | 5/1992 | Guglielmetti et al. | 252/586 |
| 5,139,707 | 8/1992 | Guglielmetti et al. | 252/586 |
| 5,446,150 | 8/1995 | Rickwood et al. | 544/71 |
| 5,446,151 | 8/1995 | Rickwood et al. | 544/71 |

FOREIGN PATENT DOCUMENTS

| | | |
|---|---|---|
| 0245020 | 11/1987 | European Pat. Off. . |
| 2647790 | 4/1994 | France . |
| 2647789 | 7/1994 | France . |
| 63-175094 | 7/1988 | Japan . |
| 63-250381 | 10/1988 | Japan . |
| 3-251587 | 11/1988 | Japan . |
| 64-30744 | 2/1989 | Japan . |
| 1-170904 | 7/1989 | Japan . |
| 2-243694 | 9/1990 | Japan . |
| 3-66692 | 2/1991 | Japan . |
| 3-81278 | 4/1991 | Japan . |
| 63-275587 | 11/1991 | Japan . |
| WO 96/04590 | 2/1996 | WIPO . |

OTHER PUBLICATIONS

Lareginie et al., Journal of Physical Organic Chemistry, vol. 9, No. 5, pp. 262–264, May 1996.

*Primary Examiner*—Richard L. Raymond
*Attorney, Agent, or Firm*—Arnold White & Durkee

[57] ABSTRACT

The new photochromic compounds according to the invention, of the spiro[indoline-[2,3']-benzoxazine] type, include at least one electron-withdrawing group attached to the benzoxazine structure in 5' or 6' position by a chain containing at least one ethylenic double bond.

Application to ophthalmic optics.

19 Claims, No Drawings

PHOTOCHROMIC SPIROOXAZINE COMPOUNDS, THEIR USE IN THE FIELD OF OPHTHALMIC OPTICS

FIELD OF THE INVENTION

The invention relates to new photochromic compounds of the spiro[indoline-[2,3']-benzoxazine] type containing at least one electron-withdrawing group attached in position 5' and/or 6' to the benzoxazine part by a divalent linking radical, containing an ethylenic double bond or a number of conjugated ethylenic double bonds, and to their use in the field of ophthalmic optics, in particular in and/or on ophthalmic lenses.

The positions 5' and 6' to which reference is made above are defined by numbering, according to the rules of international nomenclature, the positions of the atoms in the spiro[indoline-[2,3']-benzoxazine] basic structural unit. This same indexing will be retained conventionally in the case of the positions of the various atoms of the basic structural unit of the compounds of the invention, whatever the substituents and condensed nuclei in this basic structural unit.

Positions 5' and 6' are more particularly shown in the formula (I) which appears in the description which follows.

Photochromism is a phenomenon which has been known for many years. A compound is said to be photochromic when this compound, irradiated by a beam of ultraviolet light, changes color and reverts to its original color as soon as the irradiation ceases.

The applications of this phenomenon are numerous, but one of the more particularly advantageous known applications relates to the field of ophthalmic optics.

Such compounds can be employed in the manufacture of lenses or glasses for spectacles with a view to filtering the luminous radiations as a function of their intensity.

The incorporation of photochromic compounds in an organic material forming, for example, an ophthalmic lens makes it possible to obtain a glass the weight of which is considerably smaller in comparison with the conventional lenses made of inorganic glass, which contain silver halides as photochromic agent. Their incorporation into organic materials has always presented technical difficulties.

Furthermore, not every compound with a photochromic property is necessarily capable of being employed in the field of ophthalmic optics. This is because the photochromic compound must meet a certain number of criteria including, among others:

- a high colorability, which is the measure of the ability of a photochromic compound to exhibit an intense color after isomerization;
- a coloring after absorption of the light making the photochromic compound, alone or in combination with other photochromic compounds, suitable for being employed in ophthalmic glasses or lenses;
- an absence of coloring or very weak coloring in the initial form;
- rapid coloring and fading kinetics;
- a photochromism which is exhibited in a widest possible temperature range, and in particular preferably between 0 and 40° C.

The organic photochromic compounds which are known and employed at present generally exhibit a photochromism which decreases when the temperature increases, with the result that the photochromism is particularly marked at temperatures close to 0° C., whereas it is much weaker, or even nonexistent, at temperatures of the order of 40° C., which are temperatures which the glasses can reach, especially when exposed to the sun.

Another problem encountered in the case of the photochromic compounds of the state of the art is their lifetime. A relatively short lifetime is found, in fact, in the case of some products of the state of the art. This is because after a certain number of coloring and bleaching cycles the photochromic compound undergoes a chemical degradation and no longer exhibits the reversible photochromic properties.

Compounds of the spiro(indoline-quinazolinoxazine) or spiro(indoline-benzo-thiazolooxazine) type have been described in U.S. Pat. No. 5,139,707 and U.S. Pat. No. 5,114,621 (R. Guglielmetti, P. Tardieu) granted in the name of Essilor.

Photochromic compounds of the spiro[indoline-[2,3']-benzoxazine] type have also been synthesized and described in Patent Application EP-0 245 020.

Document JP-A-03 251 587 describes photochromic compounds of 6'-substituted spiro[indoline-[2,3']-benzoxazine] structure.

Document WO-96/04590 describes photochromic compounds of spiro[indoline-[2,3']-benzoxazine] structure which have a cyano or phenylsulfonyl group in 6' position.

The compounds of the document WO-96/04590 exhibit a strong colorability, in their open form, in the visible region. Their colors are blue-green. In their colored form they exhibit absorption maximum wavelengths ranging as far as 659 nm. In addition, in their closed form, the photochromic compounds of this document exhibit a shift of their absorption bands in the region of the UV/visible radiations.

SUMMARY OF THE INVENTION

The subject of the present invention is new photochromic compounds exhibiting characteristics which are improved in comparison with the compounds of the above prior art, and especially in the case of some of them, absorption maximum wavelength values (open form) which are higher than in the case of the compounds of document WO 96/04590.

In their closed form the photochromic compounds of the invention also exhibit a shift of their absorption bands toward the UV/visible.

Another subject of the present invention is such photochromic compounds in which the photochromism is exhibited over a wide temperature range preferably running from 0° C. to 40° C. and more particularly at least up to 35° C., with excellent coloring-bleaching kinetics at 35° C.

Another subject of the present invention is optical and ophthalmic articles such as glasses or lenses incorporating these new photochromic compounds or coated with coating compositions comprising these new photochromic compounds.

Another subject of the invention is compositions intended to be employed for coating optical or ophthalmic articles, in particular ophthalmic lenses, or their incorporation into these articles.

Other subjects of the invention will appear on reading the description and the examples which follow.

The photochromic compounds in accordance with the invention are compounds including a spiro[indoline-[2,3']-benzoxazine] structure, containing at least one, preferably two, electron-withdrawing groups attached in position 5' or 6' to the spiro[indoline-[2,3']benzoxazine] structure by a divalent linking radical containing an ethylenic double bond or several conjugated ethylenic double bonds, preferably 1 to 4 ethylenic double bonds and, better, one or two ethylenic double bonds.

An electron-withdrawing group is a group that attracts electron density. The group in question may be of inductive-attracting or mesomeric-attracting type.

The presence of the electron-withdrawing group(s) attached in position 5' and/or 6' by the divalent linking radical as defined above entails a bathochromic shift in the $\lambda_{max}$ (absorption maximum wavelength of the open form of the photochromic compound), that is to say a shift toward the long wavelengths. The resulting color of the photochromic compound in its open form will therefore be shifted toward the green, a color sought after for an ophthalmic application.

Overall, the bathochromic shift will be proportionately greater the higher the attracting effect exerted via the divalent linking radical on the benzoxazine fragment.

In particular, the attracting effect exerted on the oxazine fragment is maximized when two electron-withdrawing groups are attached at the chain end of the divalent linking radical.

In general, any electron-withdrawing group attached at the chain end of the linking radical will give rise to the desired bathochromic effect. It is preferable, however, to choose powerful electron-with-drawing groups.

Reference will be made advantageously to the tables in the classical works which establish the classification of various substituents according to their electron-withdrawing character.

For example, reference may be made to the classification established by the Hammett scale (p. 145–147—The Chemist's companion, A. J. Gordon, R. A. Ford; John Wiley & Sons, 1972).

Electron-withdrawing groups exhibiting a para a value higher than or equal to 0.2, and, better still, higher than or equal to 0.3, with reference to the Hammett scale, will preferably be chosen.

DETAILED DESCRIPTION

The preferred photochromic compounds in accordance with the invention can be denoted by the general formula:

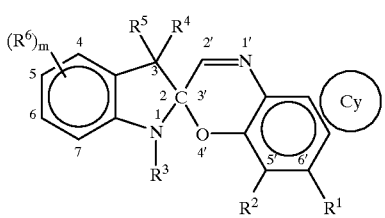

(I)

in which:
a) one of the radicals $R^1$ and $R^2$ is a radical of formula:

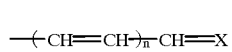

(II)

in which n is an integer from 0 to 3 inclusive, preferably equal to 0 or 1, X is a radical

where $R^a$ and $R^b$ denote, independently of one another, a hydrogen atom, an alkyl, aryl, alkylaryl, arylalkyl or heteroaryl radical or an electron-withdrawing group, at least one of $R^a$ and $R^b$, preferably both, being an electron-withdrawing group, the other of the radicals $R^1$ and $R^2$ is chosen from the substituents which can be denoted by $R^6$, defined below, and preferably from hydrogen atoms and alkyl, aryl, alkylaryl or arylalkyl groups;

b) $R^3$ is
  (i) a $C_1$–$C_{16}$ alkyl group optionally substituted by one or more hydroxyl, halogen, aryl, alkoxy, acyloxy, acryloyloxy, methacryloyloxy or vinyl substituents,
  (ii) a vinyl, allyl, phenyl or arylalkyl group or phenyl mono- or disubstituted by $C_1$–$C_6$ alkyl or alkoxy substituents or one or more halogen atoms,
  (iii) an optionally substituted alicyclic group,
  (iv) an aliphatic hydrocarbon group containing in its chain one or more heteroatoms chosen from O, N and S;

c) $R^4$ and $R^5$ are, independently of one another, a $C_1$–$C_8$ alkyl or phenyl group or phenyl mono- or disubstituted by $C_1$–$C_4$ alkyl and/or $C_1$–$C_5$ alkoxy groups, or are combined to form a cyclic chain of 6 to 8 carbon atoms;

d) $R^6$ denotes
  (i) a hydrogen atom, an $NR^7R^8$ amine functional group where $R^7$ and $R^8$ denote, independently of one another, a hydrogen atom or an alkyl, cycloalkyl, phenyl or substituted phenyl group or $R^7$ and $R^8$ are combined to form a cycloalkyl, optionally substituted and containing one or more heteroatoms,
  (ii) an $R^9$, $OR^9$, $SR^9$, $COR^9$ or $COOR^9$ group in which $R^9$ denotes a hydrogen atom or a $C_1$–$C_6$ alkyl, aryl or heteroaryl group,
  (iii) a halogen atom, a $C_1$–$C_4$ monohaloalkyl group or a $C_1$–$C_4$ polyhaloalkyl group,
  (iv) —$NO_2$, —CN or —SCN,
  (v) acrylic, methacrylic, vinyl or allyl polymerizable groups,
and m is an integer from 1 to 4;

e) Cy is an aromatic hydrocarbon ring or an aromatic heterocyclic ring containing 4 to 7 chain links and preferably 5 or 6 chain links, the heterocyclic ring containing one or more intracyclic heteroatoms chosen from nitrogen, oxygen and sulfur, it being possible for these rings and heterocyclic rings to be substituted by one or more alkyl, aryl, $(CH_2)_xOR^{10}$, —$SR^{10}$, —$COR^{10}$ or $COOR^{10}$ groups in which $R^{10}$ denotes a hydrogen atom or an aryl group and x is an integer from 0 to 10; an amino group of formula $NR^{11}R^{12}$ in which $R^{11}$ and $R^{12}$ denote independently of one another a hydrogen atom, an alkyl group, a cycloalkyl group or an aryl group, it being possible for $R^{11}$ and $R^{12}$ to form with the nitrogen atom a heterocyclic ring containing 4 to 7 chain links and capable of additionally containing one or more intracyclic heteroatoms chosen from N, S and O, an $NO_2$, —CN, —SCN group; $SO_3R^{13}$ where $R^{13}$ denotes hydrogen or an alkali metal; $SO_2R^{14}$ where $R^{14}$ is a phenyl or tolyl group or an acrylic, methacrylic, vinyl or allyl polymerizable group, or else Cy is condensed with an aromatic or cycloalkyl nucleus.

In the abovementioned formula an alkyl group preferably denotes a group containing 1 to 6 carbon atoms, a cycloalkyl group preferably denotes a group containing 3 to 7 carbon atoms, the aryl group preferably denotes a phenyl group, halogen preferably denotes chlorine, bromine or fluorine, and the polyhaloalkyl group preferably denotes the $CF_3$ group.

Methyl, ethyl, n-propyl, isopropyl and n-butyl groups may be mentioned among the recommended alkyl groups.

The benzyl group may be mentioned among the recommended arylalkyl groups.

Preferably, one of the radicals $R^1$ or $R^2$ is a hydrogen atom and the other is a radical of formula:

$$-(CH=CH)_n-CH=X \qquad (II)$$

in which X is a radical $$C\begin{matrix}\diagup R^a \\ \diagdown R^b\end{matrix},$$

n is an integer from 0 to 3, preferably equal to 0 or 1, and at least one of the groups $R^a$ and $R^b$ is an electron-withdrawing group and the other is a hydrogen atom or an alkyl, aryl, alkylaryl or arylalkyl radical.

$R^a$ and $R^b$ are preferably both electron-withdrawing groups and, in particular, $R^a$ and $R^b$ are both cyano groups.

When only one of $R^a$ and $R^b$ is an electron-withdrawing group, the other is preferably a hydrogen atom or an alkyl radical, preferably a $C_1$–$C_5$ alkyl radical such as methyl, ethyl, propyl and n-butyl.

Among the electron-withdrawing groups which are suitable for the present invention there may be mentioned the groups:

—$NO_2$, quaternary ammonium, —CN, —$SO_3R^{15}$, —$SO_2R^{15}$,

—$COOR^{15}$, —$\underset{\parallel}{\underset{O}{C}}R^{15}$, —CHO,

—$SO_2$—⟨phenyl⟩$(R_{16})_{m'}$, —$\underset{\parallel}{\underset{O}{C}}$—⟨phenyl⟩$(R_{16})_{m''}$, —$\underset{\parallel}{\underset{O}{CO}}$—⟨phenyl⟩$(R_{16})_{m'''}$, and $C_tF_{2t+1}$, in which:

$R_{15}$ is chosen from the list of the substituents which $R^3$ may denote under (i), (iii) and (iv), $R^{16}$ is chosen from the list of substituents which $R^6$ may denote under (i), (ii), (iii) and (iv), m', m" and m'" may, independently of one another, assume integral values from 1 to 5 (inclusive), and t is an integer from 1 to 6 inclusive.

$R^3$, $R^4$ and $R^5$ preferably denote hydrogen or a $C_1$–$C_5$ alkyl radical and more particularly a methyl radical.

That of $R^1$ and $R^2$ which is not a radical of formula (II) is preferably a hydrogen atom or a $C_1$–$C_5$ alkyl radical and in particular a methyl.

The preferred aromatic hydrocarbon rings denoted by Cy are 5- or 6-membered, in particular 6-membered rings, optionally substituted by one or more alkyl groups, preferably $C_1$–$C_5$.

The aromatic heterocyclic ring Cy is denoted more particularly by the formula (III):

$$\begin{matrix}(Z^1)_p\text{—}(Z^2)_q\\ \diagdown\\ \qquad\qquad C\text{—}R^{17}\\ \diagup\\ \text{—}(Z^3)_r\end{matrix} \qquad (III)$$

in which:

$Z^1$, $Z^2$ and $Z^3$ denote, independently of one another, a group $CR^{18}$ in which $R^{18}$ denotes hydrogen, a $C_1$–$C_6$ alkyl group or a phenyl group, the carbon atom being attached to one of the neighboring atoms by a double bond; a nitrogen atom attached to one of the neighboring atoms by a double bond; an oxygen or sulfur atom; p, q and r being integers equal to 0 or 1;

$R^{17}$ denotes hydrogen, a $C_1$–$C_6$ alkyl group, a phenyl group, or $R^{17}$ and $Z^2$ or $R^{17}$ and $Z^3$ may jointly form a ring containing 5 or 6 aromatic or nonaromatic, preferably benzenic chain links, or a naphthalene nucleus optionally substituted by one or more groups $(R^{19})_s$, $R^{19}$ having the meaning of any one of groups $R^4$ and $R^5$ as defined above and s having an integral value from 1 to 4 when a benzene ring is present or from 1 to 6 when a naphthalene ring is present; $Z^1$, $Z^2$, $Z^3$ and $CR^{17}$ being chosen so as to ensure the aromaticity of the condensed heterocyclic ring.

The heterocyclic nuclei which are particularly preferred are chosen from the groups of formula (III) in which p is equal to zero, $Z^2$ denotes O, S or N and $Z^3$ denotes $CR^{17}$ where $Z^2$ denotes $CR^{18}$ and $Z^3$ denotes O, S or N, $R^{17}$ and $R^{18}$ having the meanings shown above, $Z^2$ preferably denoting O or S.

Other preferred compounds are those in which p+q+r=3 and at least one of the groups $Z^1$, $Z^2$ and $Z^3$ denotes N.

Among the aromatic rings which may be denoted by Cy there may be mentioned benzene, hydroxybenzenes, alkoxybenzenes such as methoxybenzene and halobenzenes such as bromobenzene. Among the aromatic heterocyclic rings which may be denoted by Cy there may be mentioned thiophene, benzothiophene, naphthothiophene, furan, pyran, isobenzofuran, pyrrole, imidazole, pyrazole, isothiazole, isoxazole, pyridine, pyrazine, pyrimidine, pyridazine, isoindole, indole, indazole, isoquinoline, quinoline, phthalazine, quinoxaline, quinazoline and cinnaline, it being optionally possible for these rings to contain one or more substituents.

The heterocyclic nuclei Cy which are more particularly preferred are chosen from the pyridine, pyrimidine, pyrazine and furan nuclei optionally condensed with an aromatic nucleus to form an optionally substituted benzofuran or thiazole ring.

The radical $R^6$ is preferably a hydrogen atom, a $C_1$–$C_5$ alkyl radical, for example a methyl, ethyl or propyl radical, or a $C_1$–$C_5$ alkoxy radical, preferably a methoxy or ethoxy radical.

Cy is preferably a 6-membered aromatic ring and very particularly a benzene ring.

Also preferably $R^2$ denotes the radical of formula (II), that is to say that the radical of formula (II) is preferably in 5' position.

Recommended photochromic compounds according to the invention correspond to the formula:

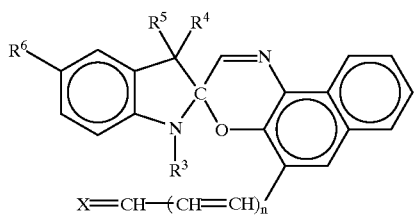

(IV)

in which $R^3$, $R^4$, $R^5$, $R^6$ and X are defined as above and n is equal to 0 or 1.

Among the particularly recommended photochromic compounds according to the invention there may be mentioned the compounds of formula:

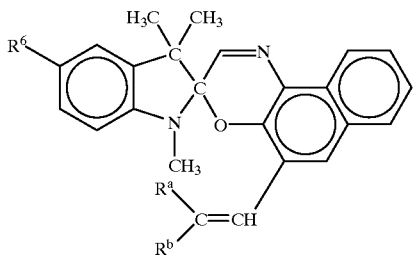

(V)

in which $R^6$=H. $R^a$=CO$_2$Me, $R^b$=H;
$R^6$=H. $R^a$=CN, $R^b$=H;
$R^6$=H. $R^a$=CN, $R^b$=p-tolyl;
$R^6$=H. $R^a$=CN, $R^b$=CF$_5$;
$R^6$=OCH$_3$, $R^a$=CN, $R^b$=C$_6$F$_5$;
$R^6$=H. $R^a$=CO$_2$C$_2$H$_5$, $R^b$=CN;
$R^6$=OCH$_3$, $R^a$=COOC$_2$H$_5$, $R^b$=CN;
$R^6$=H. $R^a$=CN, $R^b$=CN;
$R^6$=OCH$_3$, $R^a$=CN, $R^b$=H;

and the compounds of formula:

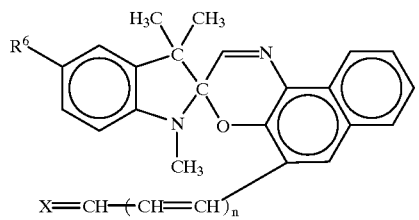

(VI)

in which $R^6$=H, X=0, n=0;
$R^6$=OCH$_3$, X=0, n=0;
$R^6$=H, X=0, n=1;
$R^6$=H, X=(COOC$_2$H$_5$) (CN), n=1.

The photochromic compounds according to the present invention can be synthesized by synthetic routes which are known per se, from corresponding compounds containing a substituent

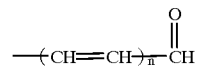

in which n is an integer from 0 to 3, preferably equal to 0 or 1, in 5' or 6' position instead of the group of formula (II), by a Wittig reaction with phosphonium salts or the appropriate phosphoranes or by a Knoevenagel reaction.

The synthetic routes for photochromic compounds according to the invention which are 5'-substituted by a group of formula (II) have been shown diagrammatically below:

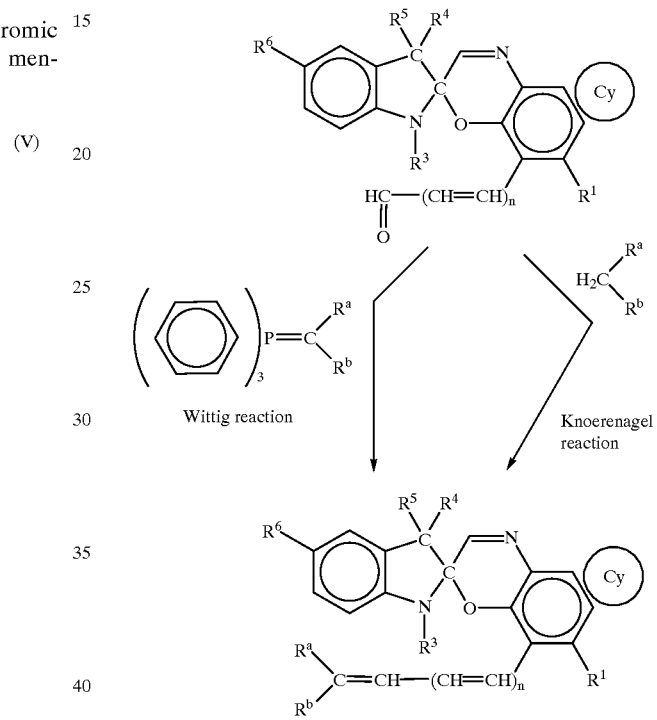

where $R^1$, $R^3$, $R^4$, $R^5$, $R^6$, $R^a$, $R^b$ and n are defined as above.

The present invention therefore also relates, as novel products, useful for the synthesis of the photochromic compounds according to the invention, to the compounds of formula:

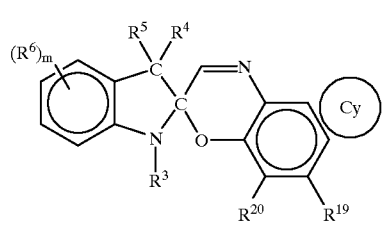

(VII)

in which one of the radicals $R^{19}$ and $R^{20}$ is a radical of formula:

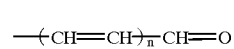

(VIII)

in which n is an integer from 0 to 3 inclusive, m an integer from 1 to 4 inclusive, preferably equal to 0 or 1, the other of the radicals $R^{19}$ and $R^{20}$ is a group as defined for $R^1$ or $R^2$ with the exception of a group of formula (II), and $R^3$, $R^4$, $R^5$ and $R^6$ and Cy are as defined above.

The preferred compounds of formula (VII) are those substituted in 5' position and in which $R^1$, $R^2$, $R^3$, $R^5$, $R^6$ and Cy have the preferred meanings indicated above.

Compounds of formula (VII) can be synthesized in a known manner by condensation of a 3- or 4-hydroxymethyl-1-nitroso-2-naphthol with the corresponding 2-methyleneindoline as described in the document U.S. Pat. No. 5,166,345 or the corresponding indoleninium in the presence of triethylamine, and then by oxidation of the compound obtained, for example with the Dess-Martin reactant to obtain the corresponding aldehydes. The preparation of the Dess-Martin reactant is described in J. Org. Chem. 1983, 48, 4155.

This synthesis can be depicted diagrammatically as follows (the case where n=0 and m=1 has been depicted).

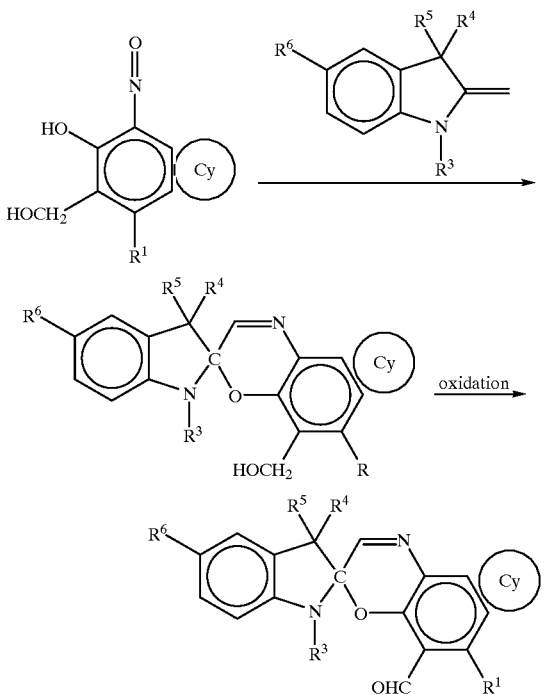

where $R^1$, $R^3$, $R^4$, $R^5$, $R^6$ and Cy have the same meaning as above.

The photochromic compounds in accordance with the invention can be employed for producing photochromic ophthalmic lenses.

The compounds in accordance with the invention can be introduced into a composition intended to be applied to or to be introduced into a transparent organic polymer material to obtain a photochromic transparent article. They can also be introduced into solid compositions such as plastic films, plates and lenses to produce materials that can be employed, especially as ophthalmic lenses, sunglasses, viewfinders, camera optics and filters.

The liquid compositions which form a subject of the invention are essentially those which contain, in dissolved or dispersed form, the compounds in accordance with the invention in a medium based on appropriate solvents for being applied to or introduced into a transparent polymer material.

Solvents that can be more particularly employed are organic solvents chosen from benzene, toluene, chloroform, ethyl acetate, methyl ethyl ketone, acetone, ethyl alcohol, methyl alcohol, acetonitrile, tetrahydrofuran, dioxane, ethylene glycol methyl ether, dimethylformamide, dimethyl sulfoxide, methylcellosolve, morpholine and ethylene glycol.

When the compounds in accordance with the invention are dispersed, the medium may also contain water.

According to another embodiment the compounds in accordance with the invention may be introduced and preferably dissolved in colorless or transparent solutions prepared from transparent polymers, copolymers or polymer mixtures in an appropriate organic solvent.

Examples of such solutions are, among others, solutions of nitrocellulose in acetonitrile, polyvinyl acetate in acetone, polyvinyl chloride in methyl ethyl ketone, polymethyl methacrylate in acetone, cellulose acetate in dimethylformamide, polyvinylpyrrolidone in acetonitrile, polystyrene in benzene and ethyl cellulose in methylene chloride.

These compositions can be applied to transparent substrates such as those made of polyethylene terephthalate, of borylated paper or of cellulose triacetate, and dried to obtain a photochromic material which can become colored in the presence of an ultraviolet radiation, and which reverts to the colorless and transparent state in the absence of the source of radiation.

The photochromic compounds of the present invention or the compositions containing them and defined above may be applied to or incorporated in a solid transparent polymerized organic material which is suitable for ophthalmic components such as ophthalmic lenses or materials useful for being employed in sunglasses, viewfinders, camera optics and filters.

As transparent solid materials which can be employed for producing ophthalmic lenses in accordance with the invention there may be mentioned polyol (allyl carbonate) polymers, polyacrylates, poly(alkyl acrylates) such as polymethyl methacrylates, cellulose acetate, cellulose triacetate, cellulose propionate acetate, cellulose butyrate acetate, poly (vinyl acetate), poly(vinyl alcohol), polyurethanes, polycarbonates, polyethylene terephthalates, polystyrenes, polystyrene-methyl methacrylate copolymers, styrene and acrylonitrile copolymers and polyvinyl butyrates.

The transparent copolymers or transparent polymer mixtures are also suitable for producing such materials.

On this topic there may be mentioned materials prepared from polycarbonates such as poly(4,4'-dioxydiphenol-2,2-propane), polymethyl methacrylate, polyol (allyl carbonate)s such as in particular diethylene glycol bis(allyl carbonate) and its copolymers such as, for example, with vinyl acetate. Particular mention may be made of the copolymers of diethylene glycol bis(allyl carbonate) and of vinyl acetate (80–90/10–20) and the copolymer of diethylene glycol bis(allyl carbonate) with vinyl acetate, cellulose acetate and cellulose propionate, cellulose butyrate (80–85/15–20).

The polyol (allyl carbonate)s are prepared by employing allyl carbonates of linear or branched, aliphatic or aromatic, liquid polyols such as bisallyl carbonate aliphatic glycols or alkylene bis(allyl carbonate)s. Among the polyol (allyl carbonate)s which may be employed to prepare the solid transparent materials that can be employed in accordance with the invention there may be mentioned ethylene glycol bis(allyl carbonate), diethylene glycol bis(2-methallyl carbonate), diethylene glycol bis(allyl carbonate), ethylene glycol bis(2-chloroallyl carbonate), triethylene glycol bis (allyl carbonate), 1,3-propanediol bis(allyl carbonate), propylene glycol bis(2-ethylallyl carbonate), 1,3-butanediol bis (allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylene bisphenol bis (allyl carbonate). The most important product consists of diethylene glycol bis(allyl carbonate), also known under the name CR39.

The quantity of photochromic compounds to be employed in accordance with the invention, either in the composition or at the time of its introduction into the solid substrate, is not critical and generally depends on the intensity of the color which the composition can impart to the material after exposure to the radiations. In general, the more photochromic compounds are added, the greater the coloring under irradiation.

In accordance with the invention a sufficient quantity is employed to impart to the treated material the property of changing color at the time of the exposure to the radiation. This quantity of photochromic compounds is generally between 0.01 and 20% by weight and preferably between 0.05 and 10% by weight relative to the total weight of the optical material or of the composition.

The photochromic compounds in accordance with the invention can also be introduced into a temporary substrate (such as a varnish forming a coating on a substrate) for transfer and can subsequently be transferred thermally in the substrate as described in particular in U.S. Pat. No. 4,286,957 or U.S. Pat. No. 4,880,667.

The present invention therefore also covers the transfer varnishes including one or more photochromic compounds according to the invention.

These compounds may be employed with other photochromic compounds such as photochromic compounds which give rise to different colors, such as yellow or red, which are known in the state of the art. Chromenes, which are well known in the state of the art can thus be employed.

Once they have been applied to ophthalmic materials or introduced into such materials, after exposure to the UV irradiations the appearance of a coloring is found, and the return to the original color or transparency when the exposure to the UV radiations is stopped.

The compounds in accordance with the invention have the advantage of allowing this change in color a large number of times, this being at very variable temperatures of between 0 and 40° C., in particular from the ambient temperature to 35° C. In their closed form, the compounds according to the invention have an absorption which is shifted toward higher wavelengths.

The following examples are intended to illustrate the invention without, however, being limiting in their nature.

EXAMPLE 1

5'-Formyl-1,3,3-trimethylspiro[indoline-2,3'-[3H]-naphtho[2,1-b][1,4]oxazine]

A solution of 0.36 g (1 mmol) of 5'-hydroxymethyl-1,3,3-trimethylspiro[indoline-2,3'-[3H]-naphtho[2,1-b][1,4]oxazine] in 30 ml of dichloromethane is added to 0.42 g (1 mmol) of Dess-Martin reactant prepared according to the method published in J. Org. Chem., 1983, 48, 4155, in solution in 60 ml of anhydrous dichloromethane. The mixture is then stirred for 1 hour at ambient temperature. 100 ml of ethyl ether are then added. The solution is then filtered and then evaporated. The product is purified by chromatography on a column of silica ($CH_2Cl_2$ eluent).

Yld=67%

M.p.=176° C.

EXAMPLE 2

5'-Formyl-5-methoxy-1,3,3-trimethylspiro[indoline-2,3'-[3H]-naphtho[2,1-b][1,4]oxazine]

This compound is prepared according to the method employed for Example 1, from 0.42 g (1 mmol) of Dess-Martin reactant and 0.39 g (1 mmol) of 5'-hydroxymethyl-5-methoxy-1,3,3-trimethylspiro[indoline-2,3'-[3H]-naphtho[2,1-b][1,4]oxazine].

Yld=72%

M.p.=171° C.

EXAMPLE 3

5'-(2-Methoxycarbonylvinyl)-1,3,3-trimethylspiro-[indoline-2,3'-[3H]-naphtho[2,1-b][1,4]oxazine]

0.34 g (1 mmol) of carbomethoxymethylene triphenylphosphorane and 0.36 g (1 mmol) of the compound of Example 1 are heated to reflux in 20 ml of dichloromethane for 18 hours. The solvent is evaporated off. The product is purified on a silica column (80/20 pentane/ethyl acetate eluent).

A mixture of cis and trans compounds is obtained. The predominant cis compound, as shown in Table I below, is isolated and investigated.

Yld=52%

M.p.=106° C.

EXAMPLE 4

5'-(2-Cyanovinyl)-1,3,3-trimethylspiro[indoline-2,3'-[3H]-naphtho[2,1-b][1,4]oxazine]

1 ml of a 50% strength sodium hydroxide solution is added to a solution of 0.36 g (1 mmol) of the compound of Example 1 and of 0.34 g (1 mmol) of cyanomethyltriphenylphosphonium chloride in 3 ml of dichloromethane. The mixture is stirred at ambient temperature for 1 hour. 10 ml of water are then added and the aqueous phase is extracted with twice 10 ml of dichloromethane. The organic phase is washed, dried and evaporated. A purification is performed on a silica column ($CH_2Cl_2$ eluent).

The product obtained is a cis and trans mixture. The predominant cis compound, as shown in Table (I) below, is isolated and investigated.

Yld=68%

M.p.=152° C.

EXAMPLE 5

5'-(2-Cyanovinyl)-5-methoxy-1,3,3-trimethylspiro-[indoline-2,3'-[3H]-naphtho[2,1-b][1,4]oxazine]

This compound is prepared according to the method employed for Example 4, from 0.39 g (1 mmol) of the compound of Example 2 and 0.34 g (1 mmol) of cyanomethyltriphenylphosphonium chloride.

Yld=33%

M.p.=140° C.

EXAMPLE 6

5'-(2-Formylvinyl)-1,3,3-trimethylspiro[indoline-2,3'-[3H]-naphtho [2,1-b][1,4]oxazine]

A solution of 0.36 g (1 mmol) of the compound of Example 1 and of 0.30 g (1 mmol) of (triphenylphosphoranylidene)acetaldehyde in 10 ml of toluene is heated to reflux for 24 hours. The solvent is then evaporated off and the mixture purified on a silica column (70/30 pentane/ether eluent).

Yld=23%

M.p.=158° C.

EXAMPLE 7

5'-(2-Cyano-2-p-tolylvinyl)-1,3,3-trimethylspiro-[indoline-2,3'-[3H]-naphtho[2,1-b][1,4]oxazine]

5 ml of a 50% strength sodium hydroxide solution are added to a solution of 0.36 g (1 mmol) of the compound of Example 1, of 0.13 g (1 mmol) of 4-methylbenzyl cyanide and of 0.05 g of polyethylene glycol 400 in 15 ml of toluene. The mixture is left at ambient temperature for 2 hours. The organic phase is separated off, washed with water, dried and evaporated. The product is purified by chromatography on a silica column ($CH_2Cl_2$ eluent)

Yld=25%

M.p.=188° C.

EXAMPLE 8

5'-(2-Cyano-2-pentafluorophenylvinyl)-1,3,3-trimethylspiro[indoline-2,3'-[3H]-naphtho[2,1-b][1,4]oxazine]

This compound is prepared according to the method employed for Example 7, from 0.36 g (1 mmol) of the compound of Example 1 and from 0.2 g (1 mmol) of 2,3,4,5,6-pentafluorophenylacetonitrile.

Yld=28%

M.p.=175° C.

EXAMPLE 9

5'-(2-Cyano-2-pentafluorophenylvinyl)-5-methoxy-1,3,3-trimethylspiro[indoline-2,3'-[3H]-naphtho[2,1-b][1,4]-oxazine]

This compound is prepared according to the method employed for Example 7, from 0.39 g (1 mmol) of the compound of Example 2 and from 0.21 g (1 mmol) of 2,3,4,5,6-pentafluorophenylacetonitrile.

Yld=18%

M.p.=219° C.

EXAMPLE 10

5'-(2-Cyano-2-ethoxycarbonylvinyl)-1,3,3-trimethylspiro-[indoline-2,3'-[3H]-naphtho[2,1-b][1,4]oxazine]

To a solution of 0.18 g (1.5 mmol) of ethyl cyanoacetate in a minimum quantity of ethanol are added 0.36 g (1 mmol) of the product of Example 1 and then two drops of piperidine. The mixture is heated at 60° C. until a precipitate appears. The precipitate obtained is filtered off, washed with ethanol and dried.

Yld=76%

M.p.=196° C.

EXAMPLE 11

5'-(2-Cyano-2-ethoxycarbonylvinyl)-5-methoxy-1,3,3-trimethylspiro[indoline-2,3'-[3H]-naphtho[2,1-b][1,4]-oxazine]

This compound is prepared according to the method employed for Example 10, from 0.39 g (1 mmol) of the compound of Example 2 and from 0.18 g (1.5 mmol) of ethyl cyanoacetate.

Yld=58%

M.p.=182° C.

EXAMPLE 12

5'-(2,2-Dicyanovinyl)-1,3,3-trimethylspiro[indoline-2,3'-[3H]-naphtho[2,1-b][1,4]oxazine]

This compound is prepared according to the method employed for Example 10, from 0.36 g (1 mmol) of the compound of Example 1 and from 0.13 g (2 mmol) of malononitrile.

Yld=42%

M.p.=208° C.

EXAMPLE 13

5'-(2,2-Dicyanovinyl)-5-methoxy-1,3,3-trimethylspiro-[indoline-2,3'-[3H]-naphtho[2,1-b][1,4]oxazine]

This compound is prepared according to the method employed for Example 10, from 0.39 g (1 mmol) of the compound of Example 2 and from 0.13 g (2 mmol) of malononitrile.

Yld=37%

M.p.=206° C.

EXAMPLE 14

5'-(4-Cyano-4-ethoxycarbonylbuta-1,3-dien-1-yl)-5-methoxy-1,3,3-trimethylspiro[indoline-2,3'-[3H]-naphtho[2,1-b][1,4]oxazine]

This compound is prepared according to the method employed for Example 10, from 0.39 g (1 mmol) of the compound of Example 6 and from 0.18 g (1.5 mmol) of ethyl cyanoacetate.

Yld=51%

M.p.=208° C.

The maximum wavelengths ($\lambda_{max}$) of the compounds of Examples 1 to 14 were measured at 25° C. (±1° C.) in solution in toluene (Carlo Eba, ACS, HPLC grade) at a concentration of $2.5 \times 10^{-5}$ M, with the aid of a spectrophotometer (Beckman DU 7500, UV-visible, diode barette detector). The solutions are irradiated in a 1-cm side rectangular quartz cell, by means of a xenon ozone-free lamp (Oriel XE XBO 150 W) powered by an Oriel (68806) amplifier.

The results are given in Table I below.

TABLE I

| MOLECULE | λmax (nm) |
|---|---|
| 1 | 631 |

TABLE I-continued

| MOLECULE | λmax (nm) |
|---|---|
| 3 (structure with CO₂Me) | 615 |
| 4 (structure with CN) | 627 |
| 6 (structure with CHO) | 634 |
| 7 (structure with CN, pTol) | 632 |
| 8 (structure with CN, C₆F₅) | 643 |
| 10 (structure with CN, CO₂Et) | 651 |
| 12 (structure with CN, CN) | 666 |
| 2 (structure with OCH₃, CHO) | 647 |

TABLE I-continued

| MOLECULE | λmax (nm) |
|---|---|
| 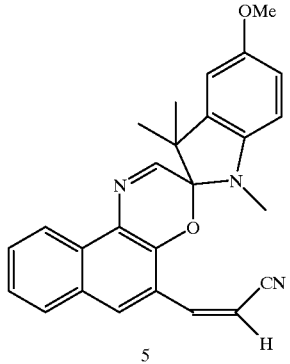 5 | 644 |
| 14 | 652 |
| 9 | 661 |
| 11 | 668 |
| 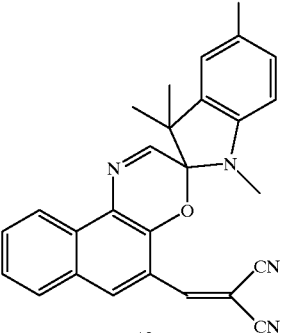 13 | 683 |

The values of $A_{eq}$ (absorbance in the photostationary state) at 35° C., at a photochromic concentration of $5\times10^{-4}$ M in toluene are measured for the photochromic compounds of Examples 8, 10, 12 and 14 and for a reference photochromic compound, 6'-cyano-1,3,3-trimethylspiro[indoline-[2,3']-[3H]naphth-[2,1,b]-[1,4]oxazine] described in Patent Application WO 96/04590.

The values of $A_{eq}$ are determined in the same experimental conditions as for the measurement of the $\lambda_{max}$, with a luminous flux power of the lamp set at 115 W/m².

The results are the following:

|  | $A_{eq}$ |
|---|---|
| Ex. 12 | 0.4 |
| Ex. 10 | 0.2 |
| Ex. 8 | 0.1 |
| Ex. 14 | 0.03 |
| 6'-Cyano comparison product | 0.03 |

It is found that the compounds of the invention generally have an $A_{eq}$ value (measured at 35° C.) higher than that of the reference compound of the most closely related prior art.

Rigid photochromic disks were produced by polymerization of a composition including, in parts by weight, 100 parts of methyl methacrylate (MMA), 2 parts of ethylene glycol dimethacrylate (EGDM), 0.03 parts of azobisisobutyronitrile (AIBN) and a photochromic compound according to the invention. The nature and the quantity (in mol %) of the photochromic compound are shown in Table II below.

The compositions are cast in an appropriate mold and then heated for 15 hours at 64° C. The temperature is then raised over 10 minutes to 83° C. and kept at this value for 8 hours. After cooling to the ambient temperature, rigid photochromic disks are recovered which have the following dimensions:

diameter: 12 mm,
thickness: 0.14 mm.

The following photochromic characteristics were determined for each disk at 35° C.:

percentage transmission of the closed form ($T_{CF}$);
percentage transmission of the open form ($T_{OF}$);
$\Delta T = T_{CF} - T_{OF}$
maximum absorption wavelength ($\lambda_{max}$)
the color under UV.

The results are given in Table II.

The irradiations were performed at 35° C. for 15 minutes with a 150 W xenon lamp, 0.57 mW/cm$^2$, 25 klux (coloring phase). The irradiation is then stopped. A fading phase is produced.

The change in the percentage transmission of each disc is measured as a function of the time during the two phases, at the $\lambda_{max}$ wavelength corresponding to the maximum absorption of the photochromic compound of the disk.

TABLE II

| Photochromic compound | Concentration in mol % | % transmission ($\lambda_{max}$) closed form | % transmission ($\lambda_{max}$) open form | $\lambda_{max}$ | ΔT | Color under UV |
|---|---|---|---|---|---|---|
|  |  | 62 | 52 | 440 | 10 |  |
| Ex. 12 | 0.057 | 74 | 32 | 666 | 42 | Light green |
| Ex. 4 | 0.16 | 85 | 56 | 627 | 29 | Blue |
| Ex. 8 | 0.11 | 71 | 35 | 643 | 36 | Dark green |
| Ex. 7 | 0.13 | 77.5 | 30 | 632 | 47.5 | Green |
| Ex. 6 | 0.16 | 71 | 46 | 634 | 25 | Yellow-green |
| Ex. 14 | 0.1 | 83.5 | 62 | 652 | 21.5 | Green |
|  | 0.1 | 86 | 57 | 647 | 29 |  |
| Ex. 2 | 0.167 | 70 | 22 | 647 | 48 | Blue |
| Ex. 5 | 0.15 | 72.5 | 42 | 644 | 30.5 | Green (blue) |
| Ex. 9 | 0.1 | 70 | 37 | 661 | 33 | Green (yellow) |
| Ex. 1 | 0.1 | 93 | 54 | 645 | 39 | Turquoise blue |
| Ex. 10 | 0.1 | 81 | 42 | 650 | 39 | Green |

We claim:

1. A photochromic compound which corresponds to general formula:

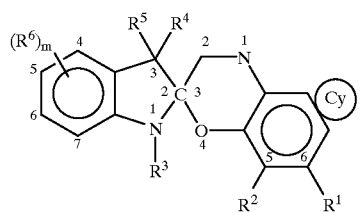

(I)

in which:
a) R$^2$ is a radical of formula:

(II)

in which n is an integer from 0 to 3 inclusive,
X is oxygen or a radical

where R$^a$ and R$^b$ denote, independently of one another, a hydrogen atom, an alkyl, aryl, alkylaryl, arylalkyl or heteroaryl radical or an electron-withdrawing group, at least one of Ra and Rb being an electron-withdrawing group, with the proviso that, when X is oxygen, n is not zero, and R$^1$ is chosen from the substituents denoted by R$^6$, defined below;
b) R$^3$ is
(i) a C$_1$–C$_{16}$ alkyl group optionally substituted by one or more acryloyloxy, hydroxyl, halogen, aryl, alkoxy, acyloxy, methacrylolyoxy or vinyl substituents,
(ii) a vinyl, allyl, phenyl or arylalkyl group or phenyl mono- or disubstituted by C$_1$–C$_6$ alkyl or alkoxy substituents or one or more halogen atoms,
(iii) an optionally substituted alicyclic group,
(iv) an aliphatic hydrocarbon group containing in its chain one or more heteroatoms chosen from O, N and S;
c) R and R$^5$ are, independently of one another, a C$_1$–C$_2$ alkyl or phenyl group or phenyl mono- or disubstituted by C$_1$–C$_4$ alkyl and/or C$_1$–C$_5$ alkoxy groups, or are combined to form a cyclic chain of 6 to 8 carbon atoms;
d) R$^6$ denotes
(i) a hydrogen atom, an NR$^7$R$^8$ amine functional group where R$^7$ and R$^8$ denote, independently of one another, a hydrogen atom or an alkyl, cycloalkyl, phenyl or substituted phenyl group or R$^7$ and R$^8$ are combined to form a cycloalkyl, optionally substituted and containing one or more heteroatoms,
(ii) an R$^9$, OR$^9$, SR$^9$, COR$^9$ or COOR$^9$ group in which R$^9$ denotes a hydrogen atom or a C$_1$–C$_6$ alkyl, aryl or heteroaryl group,
(iii) a halogen atom, a C$_1$–C$_4$ monohaloalkyl group or a C$_1$–C$_4$ polyhaloalkyl group,
(iv) —NO$_2$, —CN or —SCN,
(v) an acrylic, methacrylic, vinyl or allyl polymerizable group;
and m is an integer from 1 to 4 inclusive;
e) Cy is an aromatic hydrocarbon ring or an aromatic heterocyclic ring containing 4 to 7 chain links the heterocyclic ring containing one or more intracyclic heteroatoms chosen from nitrogen, oxygen and sulfur, it being possible for these rings and heterocyclic rings to be substituted by one or more alkyl, aryl, (CH$_2$)$_x$OR$^{10}$, —SR$^{10}$, —COR$^{10}$ or COOR$^{10}$ groups in which R$^{10}$ denotes a hydrogen atom or an aryl group and x is an integer from 0 to 10; an amino group of formula NR$^{11}$R$^{12}$ in which R$^{11}$ and R$^{12}$ denote independently of one another a hydrogen atom, an alkyl group, a cycloalkyl group or an aryl group, it being possible for R$^{11}$ and R$^{12}$ to form with the nitrogen atom a heterocyclic ring containing 4 to 7 chain links and capable of additionally containing one or more intracyclic heteroatoms chosen from N, S and O, an NO$_2$, —CN, —SCN group; SO$_3$R$^{13}$ where R$^{13}$ denotes hydrogen or an alkali metal; SO$_2$R$^{14}$ where R$^{14}$ is a phenyl or tolyl group or an acrylic, methacrylic, vinyl or allyl polymerizable group, or else Cy is condensed with an aromatic or cycloalkyl nucleus.

2. The compound as claimed in claim 1, wherein in the group of formula (II) n is equal to 0 or 1.

3. The compound as claimed in claim 1, wherein the electron-withdrawing group is:

—$NO_2$, quaternary ammonium, —CN, —$SO_3R^{15}$, —$SO_2R^{15}$,

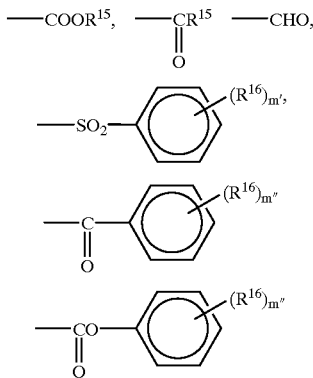

or $C_tF_{2t+1}$, in which:

$R^{15}$ is selected from the group consisting of substituents denoted by $R^3$ under (i), (iii) and (iv), $R^{16}$ is selected from the group consisting of substituents denoted by $R^6$ under (i), (ii), (iii) and (iv), m', m'' and m''' are, independently of one another, integral values from 1 to 5 and t is an integer from 1 to 6.

4. The compound as claimed in claim 1, wherein, in the radical of formula (II), $R^a$ and $R^b$ are both an electron-withdrawing group.

5. The compound as claimed in claim 4, wherein $R^a$ and $R^b$ are both cyano groups.

6. The compound as claimed in claim 1 wherein Cy is an aromatic heterocyclic ring of formula:

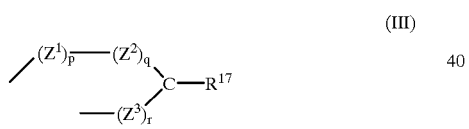

in which:

$Z^1$, $Z^2$ and $Z^3$ denote, independently of one another, a group $CR^{18}$ in which $R^{18}$ denotes hydrogen, a $C_1$–$C_6$ alkyl group or a phenyl group, the carbon atom being attached to one of the neighboring atoms by a double bond; a nitrogen atom attached to one of the neighboring atoms by a double bond; an oxygen or sulfur atom; p, q and r being integers equal to 0 or 1;

$R^{17}$ denotes hydrogen, a $C_1$–$C_6$ alkyl group, a phenyl group, or a structure wherein $R^{17}$ and $Z^2$ or $R^{17}$ and Z3 jointly form a ring containing 5 or 6 aromatic or nonaromatic chain links or a naphthalene nucleus optionally substituted by one or more groups $(R^{19})_s$, $R^{19}$ having the meaning of any one of groups $R^4$ and $R^5$ as defined above and s having an integral value from 1 to 4 when a benzene ring is present or from 1 to 6 when a naphthalene ring is present; $Z^1$, $Z^2$, $Z^3$ and $CR^{17}$ being chosen so as to ensure the aromaticity of the condensed heterocyclic ring.

7. The compound as claimed in claim 1, wherein $R^1$ is a hydrogen atom or a $C_1$–$C_5$ alkyl radical;

$R^3$, $R^4$ and $R^5$ denote a hydrogen atom or a $C_1$–$C_5$ alkyl radical;

$R^6$ is a hydrogen atom, a $C_1$–$C_5$ alkyl radical or a $C_1$–$C_5$ alkoxy radical; and Cy is an aromatic hydrocarbon ring chosen from benzene, a hydroxybenzene, an alkoxybenzene or a halobenzene.

8. The compounds as claimed in claim 1 which correspond to the general formula:

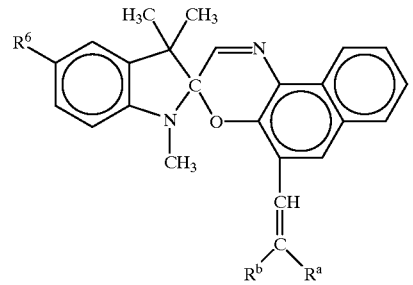

which:

$R^6$=H, $R^a$=$CO_2Me$, $R^b$=H;
$R^6$=H, $R^a$=CN, $R^b$=H;
$R^6$=H, $R^a$=CN, $R^b$=p-tolyl;
$R^6$=H, $R^a$=CN, $R^b$=$CF_5$;
$R^6$=$OCH_3$, $R^a$=CN, $R^b$=$C_6F_5$;
$R^6$=H, $R^a$=$CO_2C_2H_5$, $R^b$=CN;
$R^6$=$OCH_3$, $R^a$=$COOC_2H_5$, $R^b$=CN;
$R^6$=H, $R^a$=CN, $R^b$=CN;
$R^6$=$OCH_3$, $R^a$=CN, $R^b$=H.

9. The compound as claimed in claim 1 which corresponds to the general formula:

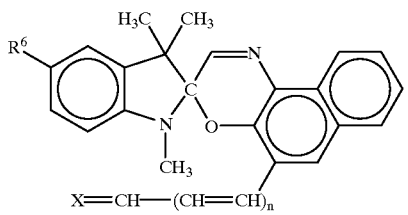

(VI)

in which:

$R^6$=H, X=O, n=1;
$R^6$=H, X=C($COOC_2H_5$) (CN), n=1.

10. The compound as claimed in claim 1 which has the formula:

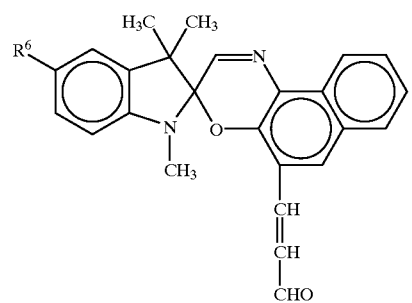

where $R^6$ denotes a hydrogen atom or —$OCH_3$.

11. A composition for the application or introduction into a transparent organic polymer material, which contains at least one photochromic compound as claimed in claim 1, in a sufficient quantity to allow the polymer material exposed to an ultraviolet radiation to change color.

12. The composition as claimed in claim 11, wherein the composition is in liquid form containing, in dissolved or dispersed form, the photochromic compounds in a medium optionally including an appropriate solvent.

13. A composition for application to or introduction into a transparent organic polymer material, which consists of a colorless or transparent solution based on transparent polymers, copolymers or polymer mixture, optionally in an appropriate organic solvent, containing at least one photochromic compound as defined in claim 1, in sufficient quantities to allow the material exposed to an ultraviolet radiation to change color.

14. A transparent solid material suitable for producing ophthalmic lenses, which comprises on the surface and/or within it at least one photochromic compound as defined in claim 1, in sufficient quantities to allow the material exposed to an ultraviolet radiation to change color.

15. The transparent solid material as claimed in claim 14, which contains 0.01 to 20% by weight of photochromic compounds.

16. The composition as claimed in claim 11, wherein the photochromic compound is employed conjointly with other photochromic compounds giving rise to different colors.

17. A transfer varnish which contains at least one compound as defined in claim 1.

18. A contact lens which contains at least one photochromic compound as defined in claim 1.

19. The transparent solid material of claim 14, wherein the photochromic compound of claim 2 is employed conjointly with other photochromic compounds giving rise to different colors.

* * * * *

UNITED STATES PATENT AND TRADEMARK OFFICE
CERTIFICATE OF CORRECTION

PATENT NO. : 6,019,914

DATED : February 1, 2000

INVENTOR(S) : Vladimir Lokshin, Karine Chamontin, Robert Guglielmetti, and Andre Samat It is certified that error appears in the above-identified patent and that said Letters Patent is hereby corrected as shown below:

In claim 1, column 19, line 35, please add a double line in the compound third from the left, between the numbers 2 and 1, as shown below:

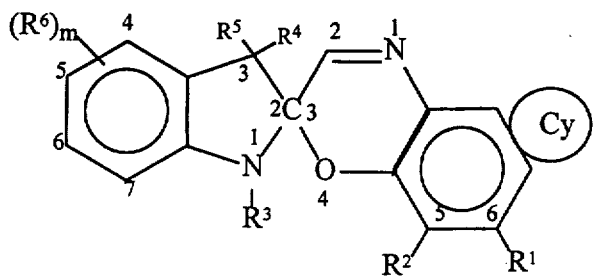

(I)

In claim 1, column 19, line 53, please delete the depiction of hydrogen atom $R^a$ and $R^b$ and insert therefor,

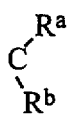

UNITED STATES PATENT AND TRADEMARK OFFICE
CERTIFICATE OF CORRECTION

PATENT NO. : 6,019,914

DATED : February 1, 2000

INVENTOR(S) : Vladimir Lokshin, Karine Chamontin, Robert Guglielmetti, and Andre Samat It is certified that error appears in the above-identified patent and that said Letters Patent is hereby corrected as shown below:

In claim 8, column 22, line 21, before "which:", please insert -- in --.

In claim 19, column 24, line 13, please delete "claim 2" and insert therefor -- claim 1 --.

Signed and Sealed this

Fourteenth Day of November, 2000

Attest:

Q. TODD DICKINSON

*Attesting Officer*    *Director of Patents and Trademarks*